(12) United States Patent
Nagano et al.

(10) Patent No.: US 8,052,862 B2
(45) Date of Patent: Nov. 8, 2011

(54) LIMITING CURRENT TYPE OXYGEN SENSOR AND METHOD OF SENSING AND MEASURING OXYGEN CONCENTRATIONS USING THE SAME

(75) Inventors: Ryouji Nagano, Tokyo (JP); Yukio Matsuki, Akita (JP); Seiki Kato, Akita (JP); Hitoshi Taimatsu, Akita (JP)

(73) Assignee: Fujikura Ltd., Tokyo (JP)

(*) Notice: Subject to any disclaimer, the term of this patent is extended or adjusted under 35 U.S.C. 154(b) by 329 days.

(21) Appl. No.: 11/768,407

(22) Filed: Jun. 26, 2007

(65) Prior Publication Data
US 2007/0295058 A1     Dec. 27, 2007

(30) Foreign Application Priority Data

Jun. 27, 2006 (JP) .................. 2006-176882
Jun. 27, 2006 (JP) .................. 2006-176883

(51) Int. Cl.
*G01N 27/41* (2006.01)
(52) U.S. Cl. ................. 205/784; 204/428
(58) Field of Classification Search .......... 204/400–435; 205/775–794.5; 73/19.01–31.07
See application file for complete search history.

(56) References Cited

U.S. PATENT DOCUMENTS

| 4,938,861 | A | 7/1990 | Kurosawa et al. | |
| 4,950,380 | A | 8/1990 | Kurosawa et al. | |
| 5,288,389 | A | 2/1994 | Yamada et al. | |
| 6,205,843 | B1* | 3/2001 | Tanaka et al. | 73/31.06 |
| 2003/0188968 | A1* | 10/2003 | Naito et al. | 204/424 |

FOREIGN PATENT DOCUMENTS

| EP | 0 442 415 A2 | 8/1991 |
| EP | 0516038 A2 | 5/1992 |
| EP | 1260814 A2 | 11/2002 |
| JP | 52-72286 A | 6/1977 |
| JP | 60-91251 A | 5/1985 |
| JP | 60-93342 A | 5/1985 |
| JP | 62-145161 A | 6/1987 |
| JP | 62-263458 A | 11/1987 |
| JP | 2-198352 A | 8/1990 |
| JP | 3-165254 A | 7/1991 |
| JP | 5-209860 A | 8/1993 |
| JP | 07218468 A * | 8/1995 |
| JP | 10-142191 A | 5/1998 |
| JP | 10185862 A | 7/1998 |
| JP | 2000-131271 A | 5/2000 |
| JP | 3373741 B2 | 11/2002 |

OTHER PUBLICATIONS

Machine translation JP 07-218468, 1995.*

* cited by examiner

*Primary Examiner* — Kaj K Olsen
*Assistant Examiner* — Susan Thai
(74) *Attorney, Agent, or Firm* — Sughrue Mion, PLLC

(57) ABSTRACT

A limiting current type oxygen sensor having a gas diffusion mechanism comprising a gas diffusion bore and an internal space communicating with the gas diffusion bore for supplying a diffusion-rate-determined gas. The gas diffusion mechanism may be configured such that an oxygen concentration gradient within the internal space satisfies the expression:

$$1/I_{lim} = (1/4\,FDC_{o2})\{(l/S) + (l_{in}/S_{in})\}$$

based on the Faraday constant (F); a diffusion coefficient (D); an oxygen concentration ($C_{o2}$); a bore area (S) of the gas diffusion bore; a bore length (l) in the axial direction of the gas diffusion bore; a distance ($l_{in}$) in the internal space between the first electrode and the inner surface opposed thereto; an effective cross section ($S_{in}$) of the internal space; and an output current value ($I_{lim}$). This makes it possible to accurately sense and measure the oxygen concentration, even at low oxygen concentrations, and achieve easy producibility and cost reducibility.

6 Claims, 5 Drawing Sheets

LIMITING CURRENT TYPE OXYGEN SENSOR AND METHOD OF SENSING AND MEASURING OXYGEN CONCENTRATIONS USING THE SAME Priority is claimed from Japanese Patent Applications No. 2006-176882 and No. 2006-176883, filed Jun. 27, 2006, the contents of which are incorporated herein by reference.

BACKGROUND

1. Field of the Invention

The present invention relates to a limiting current type oxygen sensor for use in sensing and measuring oxygen concentrations and a method of sensing and measuring oxygen concentrations using the same.

2. Description of the Related Art

A limiting current type oxygen sensor may use an ion conductor composed of, for example, stabilized zirconia of a solid electrolyte with an additive of yttrium oxide ($Y_2O_3$), (yttria stabilized zirconia: YSZ), as conventionally known. FIG. 10 is a schematic diagram showing a structure of a conventional limiting current type oxygen sensor. As shown in FIG. 10, a general, conventional limiting current type oxygen sensor 100 includes an ion conductor 101 of a solid electrolyte with an anode 102 and a cathode electrode 103 of porous material formed on both sides thereof to apply a monitor voltage across them. A gas diffusion mechanism, with gas diffusion bores 104, 105 and an internal space 106a to supply a diffusion-rate-determined gas to one electrode 103, is formed in a cap 106, which is attached to the ion conductor.

A heater 107 is provided on the outside of the cap 106 to set the ion conductor 101 at a monitor temperature of several 100° C. The heater 107 is connected to a lead wire 108. The gas diffusion bore 104 is formed through the cap 106 toward the electrode 103 while the gas diffusion bore 105 is formed through the cap along the surface of the electrode 103. Widely used limiting current type oxygen sensors are of the type that do not include one of the gas diffusion bores 105, 106, for example, the gas diffusion bore 105 formed therein.

The limiting current type oxygen sensor 100 is structured such that application of the monitor voltage across the electrodes 102, 103 allows an output current to flow in the ion conductor 101 in proportion to the voltage while the voltage is low. The limiting current type oxygen sensor 100 also has a characteristic that the output current saturates in time as the monitor voltage is elevated. The output current in the saturation region is called a limiting current. The intensity of the limiting current has a relationship to the oxygen concentration. Therefore, the limiting current type oxygen sensor 100 makes it possible to sense and measure an oxygen concentration from a limiting current value obtained in accordance with the monitor voltage.

The current flowing in the ion conductor 101 of the limiting current type oxygen sensor 100 is based on the migration of oxygen ions and has a current value that depends on the voltage and the temperature. Therefore, the limiting current type oxygen sensor 100 is set at a monitor temperature of around 400-500° C. and voltage-driven. Usually, the monitor temperature is set by providing the heater 107 on the cap 106 or a body portion of the limiting current type oxygen sensor 100, and energizing it.

Such a limiting current type oxygen sensor 100 is driven through a method of applying the monitor voltage across the electrodes 102, 103 while the heater 107 is always energized in many cases (see Patent Document 1: Japanese Patent No. 3373741, for example). In order to increase the output current value on sensing and measuring a lower oxygen concentration, the conventional limiting current type oxygen sensor 100 thus configured is provided with a gas diffusion mechanism that includes not only the gas diffusion bore 104 but also the gas diffusion bore 105 formed through the cap 106.

In the limiting current type oxygen sensor 100 provided with the gas diffusion mechanism structured to include bore portions such as the gas diffusion bores 104, 105 formed through the cap 106, the gas diffusion mechanism is configured to satisfy the condition of the following expression (1) to measure an oxygen concentration:

[EXPRESSION 1]

$$IL = \frac{-4FDSP}{RTL}\ln\left(1 - \frac{P_{O2}}{P}\right) \quad (1)$$

as a relation among the Faraday constant (F); a diffusion coefficient (D); a bore area (S) of the bore portion; a total gas pressure (P); a gas constant (R); a temperature (T); a bore length (L) of the bore portion; a partial oxygen pressure ($P_{o2}$); and an output current value (IL).

In such a limiting current type oxygen sensor, the gas diffusion mechanism may be configured such that the distance in the internal space between the electrode and an inner surface opposed thereto, that is, the thickness of the internal space 106a in the axial direction of the gas diffusion bore 104 is made smaller than the bore diameter of the gas diffusion bore 104. In this case, the output current value exhibits the following characteristic illustrated in FIG. 11. FIG. 11 is a graph showing a characteristic of voltage (V)-current (I) in the conventional limiting current type oxygen sensor of such the type. As shown in FIG. 11, if the thickness of the internal space in the gas diffusion mechanism of the limiting current type oxygen sensor is smaller than the bore diameter of the gas diffusion bore, the relation between the bias voltage (Vs) and the output current (Is) in the sensor has the characteristic represented by solid line 111. Namely, if the thickness of the internal space is smaller, oxygen molecules diffused through the gas diffusion bore into the internal space are diffusion-rate-determined also in the internal space before reaching the end of the cathode electrode. Therefore, a flat zone 112 on the solid line 111 exhibits a larger vertical tilt (a non constant value) as a characteristic. Therefore, in the conventional limiting current type oxygen sensor, the limiting current value in accordance with the monitor voltage is represented by such a characteristic, and the oxygen concentration is sensed and measured based on this value. Thus, conventional limiting current type oxygen sensors with a smaller thickness of the internal space have the characteristic of the flat zone with the larger tilt in a voltage-current relation. Consequently, ripples, fluctuations or variations in the monitor voltage deteriorate the accuracy of sensing the limiting current value and make it difficult to obtain the limiting current of an accurate value.

In the above-described conventional limiting current type oxygen sensor 100, sensing and measuring a lower oxygen concentration requires the formation of a new gas diffusion bore 105 through the cap 106 in addition to the gas diffusion bore 104. This requires a larger number of process steps in the process of producing the limiting current type oxygen sensor 100 and complicates the sensor structure itself, resulting in an increased production cost.

Further, in the limiting current type oxygen sensor 100 the new gas diffusion bore 105 is formed through the cap along the surface of the electrode 103 (the electrode surface) on the ion conductor 101. Therefore, compared with the type that includes no gas diffusion bore 105 formed therein, a larger variation in production accuracy may be caused easily, depending on the process accuracy. As a result, the variation in tilt characteristic is caused and the measurement accuracy is not stabilized.

In addition, the bore diameter of the gas diffusion bore 104 may be enlarged, instead of the gas diffusion bore 105 as in the conventional limiting current type oxygen sensor described in the above Patent Document 1, and no gas diffusion bore 105 is provided. In such a sensor, within a limiting current region with oxygen concentrations of 1% or below, the limiting current value can not satisfy the condition of the above expression (1). Accordingly, it is not possible to sense and measure an accurate oxygen concentration.

SUMMARY OF EXEMPLARY EMBODIMENTS OF THE INVENTION

The present invention has been made in consideration of such problems and has an object to provide a limiting current type oxygen sensor capable of improving the accuracy of sensing a limiting current value. The present invention has another object to provide a limiting current type oxygen sensor capable of sensing and measuring an oxygen concentration accurately and excellently even at a lower oxygen concentration and of being easily producible, preventing variations in the above described tilt characteristic, and reducing costs. It also provides a method of sensing and measuring oxygen concentrations using the same.

One embodiment the present invention provides a limiting current type oxygen sensor, comprising an ion conductor composed of a solid electrolyte; a porous electrode pair provided on the ion conductor to apply an electric field therebetween; a gas diffusion mechanism configured to supply a diffusion-rate-determined gas to a face of one electrode of the electrode pair; and a heater arranged to heat said ion conductor, wherein the gas diffusion mechanism includes an internal space in contact with the face of the one electrode of said electrode pair, and a gas diffusion bore formed to communicate the internal space with the outside of the sensor, wherein the gas diffusion mechanism is formed such that a distance in the internal space between the electrode and an inner surface opposed thereto is greater than or equal to the bore diameter of the gas diffusion bore. The gas diffusion mechanism may include a plurality of said gas diffusion bores, and internal space communicating with the plurality of gas diffusion bores, wherein the gas diffusion mechanism is formed such that the distance in the internal space is made equal to or greater than the sum of all of the diameters of the plurality of gas diffusion bores, or a value calculated from an effective cross section of the plurality of gas diffusion bores.

In another embodiment the present invention provides a limiting current type oxygen sensor, comprising anion conductor composed of a solid electrolyte; a porous electrode pair provided on the ion conductor to apply an electric field therebetween; a gas diffusion mechanism configured to supply a diffusion-rate-determined gas to a face of one electrode of the electrode pair; and a heater arranged to heat the ion conductor, wherein the gas diffusion mechanism includes an internal space in contact with the face of the one electrode of the electrode pair, and a gas diffusion bore formed to communicate the internal space with the outside of the sensor, wherein the gas diffusion mechanism is configured such that an oxygen concentration gradient within the internal space satisfies the following expression:

$$1/I_{lim} = (1/4FDC_{o2})\{(l/S) + (l_{in}/S_{in})\}$$

which is based on a relation among the Faraday constant (F); a diffusion coefficient (D); an oxygen concentration ($C_{o2}$); a bore area (S) of the gas diffusion bore; a bore length (l) in the axial direction of the gas diffusion bore; a distance ($l_{in}$) in the internal space between the electrode and the inner surface opposed thereto; an effective cross section ($S_{in}$) of the internal space; and an output current value ($I_{lim}$). The gas diffusion mechanism may be formed such that the distance in the internal space between the electrode and the inner surface opposed thereto is greater than or equal to the bore diameter of the gas diffusion bore. The gas diffusion mechanism may be configured such that the bore area (S) and the bore length (l) of the gas diffusion bore have a ratio (S/l) of 50-250 µm therebetween.

The present invention also provides a method of sensing and measuring oxygen concentrations using a limiting current type oxygen sensor, the sensor including an ion conductor composed of a solid electrolyte, a porous electrode pair provided on the ion conductor to apply an electric field therebetween, a gas diffusion mechanism configured to supply a diffusion-rate-determined gas to a face of one electrode of the electrode pair, and a heater arranged to heat the ion conductor, the method comprising forming in the gas diffusion mechanism an internal space to contact with the face of the one electrode of the electrode pair, and a gas diffusion bore to communicate the internal space with the outside of the sensor; and sensing and measuring an oxygen concentration by executing a calculation such that an oxygen concentration gradient within the internal space satisfies the condition of the following expression:

$$1/I_{lim} = (1/4FDC_{o2})\{(l/S) + (l_{in}/S_{in})\}$$

which is based on a relation among the Faraday constant (F); a diffusion coefficient (D); an oxygen concentration ($C_{o2}$); a bore area (S) of said gas diffusion bore; a bore length (l) in the axial direction of the gas diffusion bore; a distance ($l_{in}$) in said internal space between the electrode and the inner surface opposed thereto; an effective cross section ($S_{in}$) of said internal space; and an output current value ($I_{lim}$).

In accordance with an embodiment of the present invention, the gas diffusion mechanism includes an internal space brought into contact with one electrode of the electrode pair, and a gas diffusion bore formed to bring the internal space into communication with the outside of the sensor. The gas diffusion mechanism is formed such that a distance in the internal space between the electrode and an inner surface opposed thereto is greater than or equal to the bore diameter of the gas diffusion bore. Therefore, it is possible to minimize the influence of diffusion-rate determinateness in the internal space in the sensor and sense an accurate limiting current value.

In accordance with another embodiment of the present invention, the gas diffusion mechanism includes an internal space brought into contact with one electrode of the electrode pair, and a gas diffusion bore formed to bring the internal space into communication with the outside of the sensor. The gas diffusion mechanism is configured such that an oxygen concentration gradient within the internal space satisfies a certain expression. Therefore, compared with the conventional case provided with a plurality of gas diffusion bores, processing the gas diffusion bore can be made easier. In addition, based on the concentration gradient that satisfies the condition of the certain expression, the oxygen concentration can be sensed and measured accurately. This makes it possible to sense and measure an oxygen concentration accurately and excellently even at a lower oxygen concentration of 1% or below and to achieve easy producibility, prevent variations in process accuracy characteristic, and reduce production costs.

DETAILED DESCRIPTION OF THE EXEMPLARY EMBODIMENTS OF THE INVENTION

Limiting current type oxygen sensors according to a first and a second embodiment of the present invention will now be described below with reference to the accompanying drawings.

First Embodiment

Figure 1:
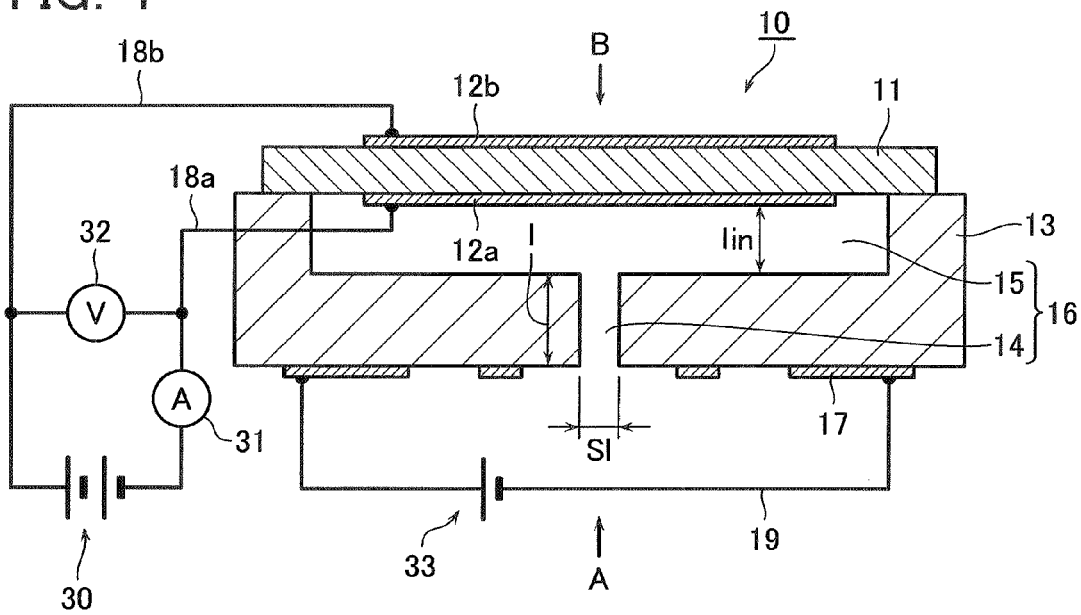
FIG. 1 is a schematic diagram showing a structure of a limiting current type oxygen sensor according to a first embodiment of the present invention.
Figure 2:
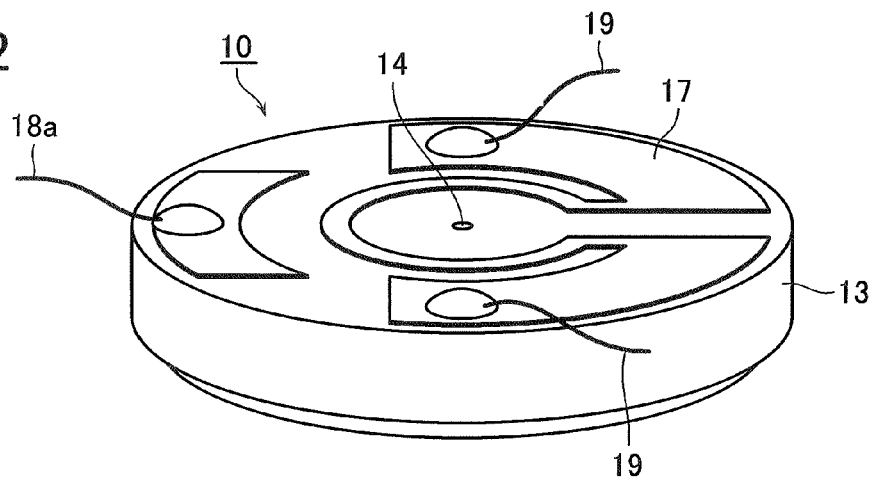
FIG. 2 is a perspective view of the limiting current type oxygen sensor seen from the direction of the arrow A in FIG. 1.
Figure 3:
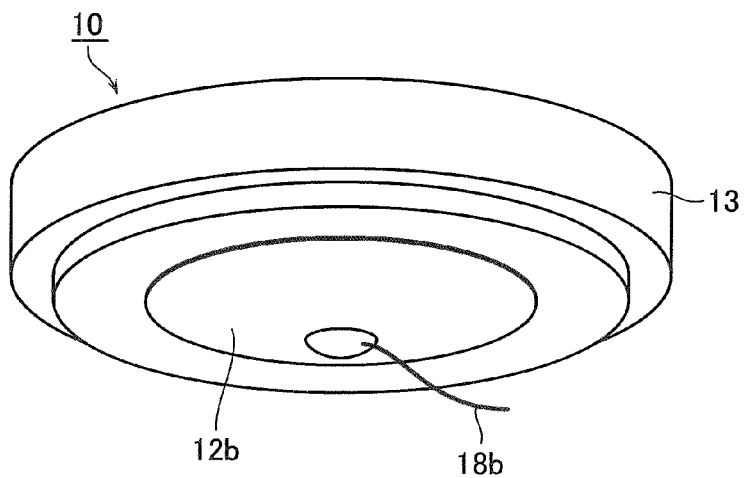
FIG. 3 is a perspective view of the limiting current type oxygen sensor seen from the direction of the arrow B in FIG. 1.

As shown in FIGS. 1-3, the limiting current type oxygen sensor 10 according to the first embodiment of the present invention includes an ion conductor 11 composed of a solid electrolyte, electrodes 12a, 12b of an electrode pair, a cap 13 provided to cover one electrode 12a of the electrodes 12a, 12b and a heater 17 arranged to heat the ion conductor 11. The electrodes 12a, 12b are composed of porous material, which are provided on the ion conductor 11 to apply an electric field therebetween.

The ion conductor 11 comprises an insulator such as stabilized zirconia that exhibits electrical conductivity in accordance with migration of internal ions at a higher temperature of several 100° C. The electrodes 12a, 12b may be composed of porous platinum (Pt) or silver (Ag) and formed on both sides of the ion conductor 11. The limiting current type oxygen sensor 10 of this example is configured such that the electrode 12a serves as a cathode electrode while the electrode 12b serves as an anode electrode.

The cap 13 may be composed of a ceramic having a bottomed cylindrical external shape and has a recessed side to be attached to the ion conductor 11. Through the center of the bottom in the bottomed cylinder of the cap 13, a single gas diffusion bore 14 is formed in the direction of the thickness. The cap 13 is attached to the ion conductor 11 in intimate contact with a side that faces the electrode 12a serving as the cathode electrode such that a gas can be supplied to the electrode 12a only through the gas diffusion bore 14. An internal space 15 is formed between the cap 13 and the side face of the ion conductor 11 facing the electrode 12a. The internal space 15 and the gas diffusion bore 14 configure a gas diffusion mechanism 16 that supplies a diffusion-rate-determined gas to the electrode 12a.

In the limiting current type oxygen sensor 10, therefore, the electrode 12a is provided in contact with the internal space 15 while the electrode 12b is provided in contact with the external atmosphere. On an outer surface of the cap 13 opposite to the side for use in attachment of the ion conductor 11 is a heater 17 provided to heat the ion conductor 11 up to a monitor temperature of, for example, around 400-500° C.

The gas diffusion bore 14 in the gas diffusion mechanism 16 is formed through the cap 13 such that it has a certain bore diameter (S1) and a certain bore length (l) in the axial direction as shown in FIG. 1. The internal space 15 in the gas diffusion mechanism 16 is formed such that it has a certain thickness in the axial direction of the gas diffusion bore 14 (lin) (specifically, a distance between a surface of the electrode 12a and an inner wall of the cap 13 located opposite to the surface). In the first embodiment, the gas diffusion mechanism 16 is configured such that the thickness (lin) of the internal space 15 is made equal to or larger than the bore diameter (S1) of the gas diffusion bore 14. The cap 13 may include a plurality of such gas diffusion bores 14 formed therein. In this case, the thickness (lin) of the internal space 15 is formed equal to or larger than the sum of all diameters of the plurality of gas diffusion bores 14, or a value previously calculated from an effective cross section of the plurality of gas diffusion bores 14.

The electrodes 12a, 12b are connected to lead wires 18a, 18b, respectively. The lead wires 18a, 18b are led out to external and connected to a power source 30 for applying a monitor voltage. The power source 30 is connected with an ammeter 31 in series and a voltmeter 32 in parallel. Further, the heater 17 is connected to a lead wire 19. The lead wire 19 is connected to a heater power source 33. The heater 17 is always energized during use from the heater power source 33 and set at a monitor temperature of around 400° C., for example.

In the limiting current type oxygen sensor 10 thus configured, the heater power source 33 supplies power to the heater 17, which resistively radiates heat to heat the limiting current type oxygen sensor 10 itself up to the monitor temperature. At the same time, the power source 30 applies a certain monitor voltage (V) across the electrodes 12a, 12b. When the monitor voltage is applied, oxygen molecules, contained in the gas present within the internal space 15 in the gas diffusion mechanism 16 surrounded by the ion conductor 11 and the cap 13, accept electrons via the electrode 12a and become oxygen ions, which enter the ion conductor 11. The oxygen ions migrate via oxygen ion holes in the ion conductor 11 and through the ion conductor 11 upward in the direction of the thickness thereof in FIG. 1. The migrated oxygen ions reach the electrode 12b where they release electrons and become oxygen molecules again, which are released to the external atmosphere. The migration of oxygen molecules causes a current (A) to flow across the electrodes 12a and 12b.

In accordance with the migration of oxygen molecules, the internal space 15 in the limiting current type oxygen sensor 10 is pressurized negative, and a gas flows therein through the gas diffusion bore 14 from the external atmosphere. The amount of the gas inflow in this case is restricted through the gas diffusion bore 14. Accordingly, in the current (I)-voltage (V) characteristic of the limiting current type oxygen sensor 10, it is possible to sense such a limiting current value that causes no variation in current even when the monitor voltage applied across the electrodes 12a, 12b is elevated.

The limiting current type oxygen sensor 10 is formed such that the thickness (lin) of the internal space 15 in the gas diffusion mechanism 16 is made equal to or larger than the bore diameter (Sl) of the gas diffusion bore 14. Accordingly, it has a structure capable of minimizing the influence of diffusion-rate-determinateness in the internal space 15 and dominating diffusion-rate-determinateness in the gas diffusion bore 14.

Figure 4:
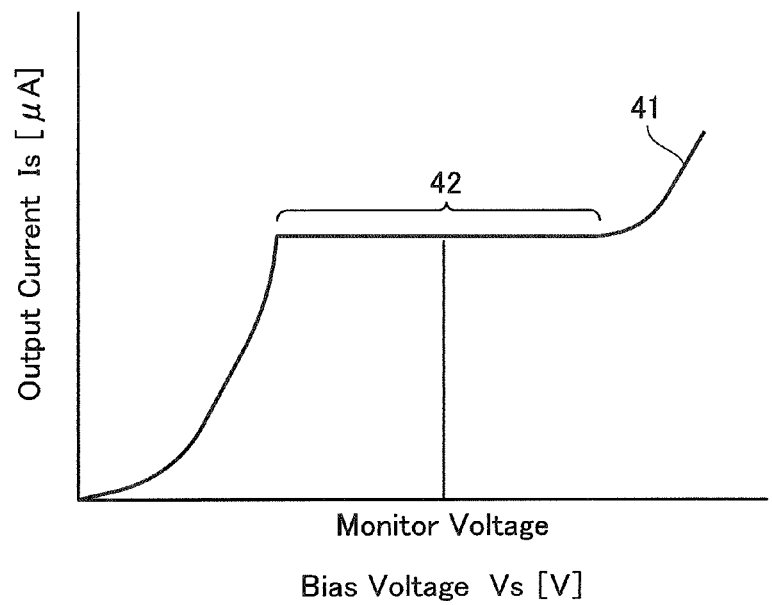
FIG. 4 is a graph showing a voltage (V)-current (I) characteristic of the limiting current type oxygen sensor.

FIG. 4 is a graph showing a voltage (V)-current (I) characteristic of the limiting current type oxygen sensor. As shown in FIG. 4, a relation between the bias voltage (Vs) and the output current (Is) in the limiting current type oxygen sensor 10 has a characteristic as represented with a solid line 41. Namely, as the thickness (lin) of the internal space 15 in the gas diffusion mechanism 16 is formed equal to or larger than the bore diameter (Sl) of the gas diffusion bore 14, the tilt on a flat zone 42 in the solid line 41 approaches zero or as close as possible. Therefore, in the limiting current type oxygen sensor 10, the output current value within the flat zone 42, or the limiting current value, exhibits a constant value even if there are external perturbations such as ripples, fluctuations or variations in the monitor voltage. Accordingly, it is possible to improve the accuracy of sensing the limiting current value. The Inventors implemented the following experiment on the relationship between the thickness (lin) of the internal space 15 in the gas diffusion mechanism 16 and the bore diameter (Sl) of the gas diffusion bore 14.

Figure 5:
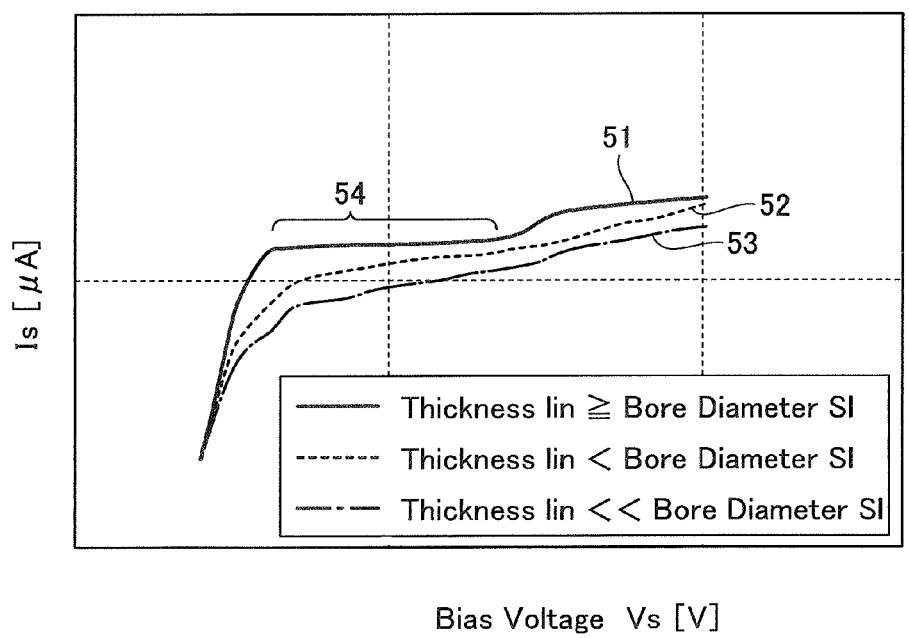
FIG. 5 is a graph showing voltage (V)-current (I) characteristics of the limiting current type oxygen sensor under an atmosphere at a certain oxygen concentration with different thicknesses of the internal space in the gas diffusion mechanism.

FIG. 5 is a graph showing voltage (V)-current (I) characteristics of the limiting current type oxygen sensor under an atmosphere at a certain oxygen concentration with different thicknesses of the internal space in the gas diffusion mechanism. As shown in FIG. 5, a solid line 51 represents a characteristic between the bias voltage (Vs) and the output current (Is) when the thickness (lin) of the internal space 15 is equal to or larger than the bore diameter (Sl) of the gas diffusion bore 14. A dashed line 52 represents a characteristic between the bias voltage (Vs) and the output current (Is) when the thickness (lin) of the internal space 15 is smaller than the bore diameter (Sl) of the gas diffusion bore 14. A chain line 53 represents a characteristic between the bias voltage (Vs) and the output current (Is) when the thickness (lin) of the internal space 15 is extremely smaller than the bore diameter (Sl) of the gas diffusion bore 14.

As represented with the solid line 51 shown in FIG. 5, the thickness (lin) of the internal space 15 equal to or larger than the bore diameter (Sl) of the gas diffusion bore 14 causes the tilt on the flat zone 54 to become almost zero or flat. In this case, the limiting current value, indicated by the output current value, also exhibits an accurate value. On the other hand, as represented with the dashed line 52 or the chain line 53, the thickness (lin) of the internal space 15 smaller or extremely smaller than the bore diameter (Sl) of the gas diffusion bore 14 causes the tilt on the flat zone 54 to become larger than that on the solid line 51. As a result, no accurate limiting current value can be obtained and an error may be caused in sensing and measuring oxygen concentrations.

Therefore, in the limiting current type oxygen sensor 10, the thickness (lin) of the internal space 15 is formed equal to or larger than the bore diameter (Sl) of the gas diffusion bore 14 to configure the gas diffusion mechanism 16. In this case, it is made possible to sense the limiting current value accurately and improve the accuracy of sensing. This is also same in the case provided with a plurality of such gas diffusion bores 14. In this case, the thickness (lin) of the internal space 15 may be formed equal to or larger than the sum of all diameters (Sl) of the plurality of gas diffusion bores 14, or a value previously calculated from an effective cross section of the plurality of gas diffusion bores 14.

As described above, in accordance with the first embodiment of the present invention, the gas diffusion mechanism 16 of the limiting current type oxygen sensor 10 includes the gas diffusion bore 14 formed through the cap 13 toward the electrode 12a, and the internal space 15 brought into communication with the gas diffusion bore 14. The thickness (lin) of the internal space 15 is formed equal to or larger than the bore diameter (Sl) of the gas diffusion bore 14. Therefore, it is possible to minimize the influence of diffusion-rate-determinateness in the internal space 15 of the limiting current type oxygen sensor 10 and sense an accurate limiting current value.

Second Embodiment

The following description is given to a limiting current type oxygen sensor and method of sensing and measuring oxygen concentrations using the same according to a second embodiment of the present invention. The limiting current type oxygen sensor according to the second embodiment has a structure almost similar to that of the first embodiment and is described with reference to FIG. 1 related to the first embodiment. Like the limiting current type oxygen sensor 10 according to the first embodiment, the limiting current type oxygen sensor according to the second embodiment comprises an ion conductor 11 composed of a solid electrolyte, electrodes 12a, 12b of an electrode pair, a cap 13 provided to cover one electrode 12a of the electrodes 12a, 12b and a heater 17 arranged to heat the ion conductor 11. The electrodes 12a, 12b are composed of porous material, which are provided on the ion conductor 11 to apply an electric field therebetween. Through the center of the bottom in the bottomed cylinder of the cap 13, a single gas diffusion bore 14 is formed in the direction of the thickness. The cap 13 is attached to the ion conductor 11 in intimate contact with a side that faces the electrode 12a serving as the cathode electrode such that a gas can be supplied to the electrode 12a only through the gas diffusion bore 14. An internal space 15 is formed between the cap 13 and the side of the ion conductor 11 facing the electrode 12a. The internal space 15 and the gas diffusion bore 14 configure a gas diffusion mechanism 16 that supplies a diffusion-rate-determined gas to the electrode 12a, like the first embodiment.

The gas diffusion bore 14 in the gas diffusion mechanism 16 is formed through the cap 13 such that it has a certain bore diameter (Sl) and a certain bore length (l) in the axial direction as shown in FIG. 1. The internal space 15 in the gas diffusion mechanism 16 is formed such that it has a certain thickness in the axial direction of the gas diffusion bore 14 (lin) (specifically, a distance between a surface of the electrode 12a and an inner wall of the cap 13 located opposite to the surface) In the second embodiment, the gas diffusion mechanism 16 is configured such that an oxygen concentration gradient within the internal space 15 satisfies the condition of a certain expression described later. Although the gas diffusion mechanism 16 is herein configured such that the thickness (lin) of the internal space 15 is made larger than the bore diameter (Sl) of the gas diffusion bore 14, the second embodiment is not limited to this configuration.

Such a limiting current type oxygen sensor 10 has a limiting current value that depends on the oxygen concentration in the atmosphere if the shape of the gas diffusion bore 14, the sensor temperature on measurement, the pressure of the atmosphere and so forth are constant. Therefore, the Inventors, based on a relation between the limiting current value and the oxygen concentration, analyzed an appropriate oxygen concentration gradient and applied it to the gas diffusion mechanism 16. Thus, the limiting current type oxygen sensor 10 is made possible to sense and measure the oxygen concentration excellently even at a lower oxygen concentration.

Figure 6:
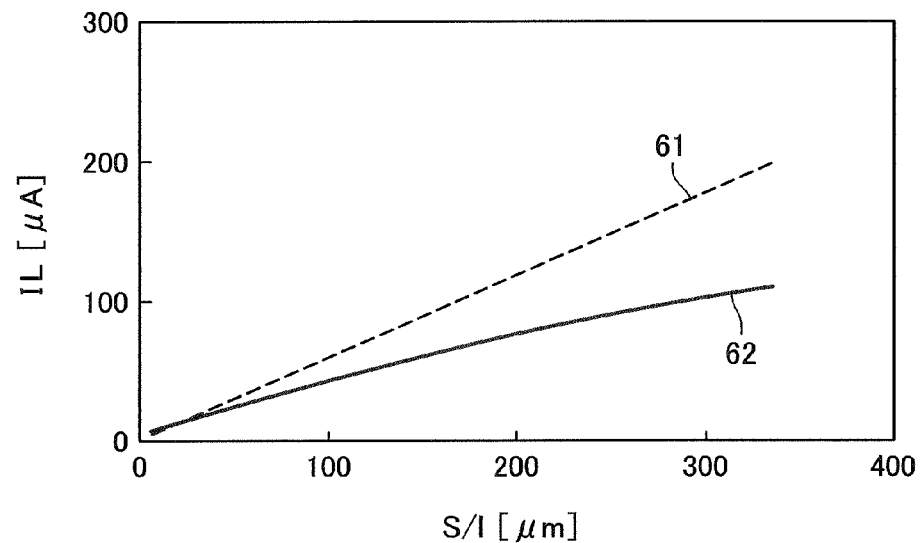
FIG. 6 is a graph representing a relation between the bore area and bore length of a gas diffusion bore and the output current in a limiting current type oxygen sensor according to a second embodiment of the present invention.
Figure 7:
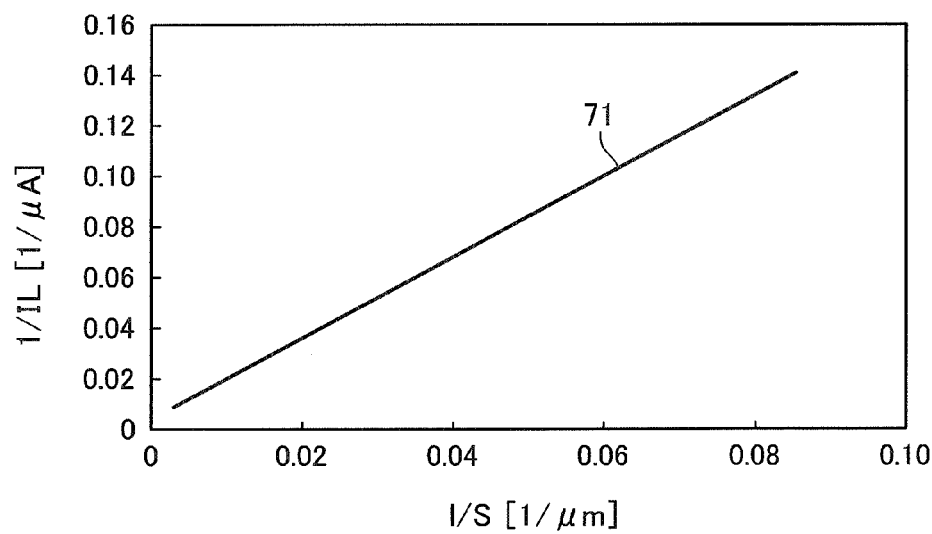
FIG. 7 is a graph representing a relation between the bore area and bore length of the gas diffusion bore and the output current in the limiting current type oxygen sensor.

FIGS. 6 and 7 are graphs each representing a relation between the bore area and bore length of the gas diffusion bore and the output current in the limiting current type oxygen sensor. First, the Inventors formed the single gas diffusion bore 14 through the center of the bottom of the cap 13 in the limiting current type oxygen sensor 10 as described above. Then, they measured the limiting current value, or the sensor output current (IL), in various environments with variations in bore area (S) and bore length (l) of the gas diffusion bore 14. As a result, it is confirmed that a ratio between the bore area (S) and the bore length (l) of the gas diffusion bore 14 (hereinafter referred to as "S/l") and the limiting current (IL) can establish a relation therebetween as shown in FIG. 6. In this case, characteristics represented with a dashed line 61 and a solid line 62 can be obtained. The dashed line 61 shows the characteristic represented by logical values calculated using the above-described conventional expression (1) while the solid line 62 shows the characteristic represented by values actually measured.

It is found as shown in FIG. 6 that the limiting current (IL) shown with the solid line 62 based on the values actually measured exhibits a smaller value, as the S/l value increases, than logical values shown with the dashed line 61 calculated using the conventional expression (1). For example, it is found that when the value of S/l falls within a range of about 50-250 μm, the S/l and the limiting current (IL) exhibit a linear relation therebetween. It is assumed from this fact that there is a concentration gradient not only in the gas diffusion bore 14 of the gas diffusion mechanism 16 but also in the internal space 15, for example, at a low oxygen concentration of 1% or below. Then, an approximated equation is analyzed to calculate the condition of the following expression (2) that satisfies the oxygen concentration gradient applied to the gas diffusion mechanism 16. If the value of S/l falls within the range of about 50-250 μm, more than one gas diffusion bore 14 may be provided.

The Inventors, apply an oxygen concentration gradient to the limiting current type oxygen sensor 10 on condition that the Faraday constant (F); a diffusion coefficient (D); an oxygen concentration ($C_{o2}$); a bore area (S) of the gas diffusion bore; a bore length (l) in the axial direction of the gas diffusion bore; a thickness ($l_{in}$) of the internal space; an effective cross section ($S_{in}$) of the internal space; and an output current value ($I_{lim}$) have the following relation,

[EXPRESSION 2]

$$\frac{1}{I_{lim}} = \frac{1}{4FDC_{O2}}\left(\frac{l}{S} + \frac{l_{in}}{S_{in}}\right) \quad (2)$$

thereby obtaining a relation between a ratio of the bore length (l) to the bore area (S) of the gas diffusion bore 14 (hereinafter referred to as "l/S") and a reciprocal of the limiting current (1/IL) as shown with a solid line 71 in FIG. 7. As a result, when the above-described S/l is equal to or lower than 50 μm, for example, the conventional expression (1) may be applied to the gas diffusion mechanism 16 for sensing and measuring oxygen concentrations though it is not practical because the value of the limiting current (IL) is too small.

The output current value ($I_{lim}$) is equivalent to the limiting current (IL). The effective cross section ($S_{in}$) of the internal space 15 is set on the basis of the assumption that a flow of oxygen molecules within the internal space 15 spreads in the form of a trapezoid from the gas diffusion bore 14 toward the electrode 12a, and through the use of around a half of the cross section of the internal space 15 and the cross section of the gas diffusion bore 14 as an index.

Figure 8:
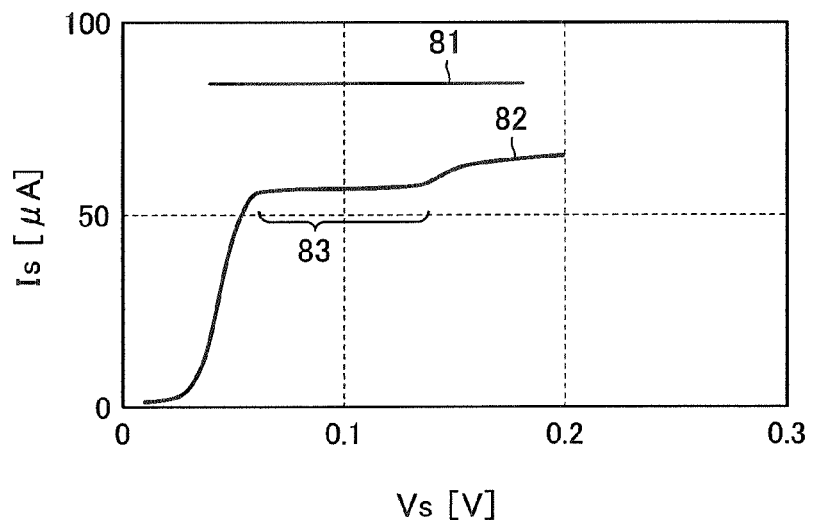
FIG. 8 is a graph showing a voltage (V)-current (I) characteristic of the limiting current type oxygen sensor.

In the limiting current type oxygen sensor 10, in which the gas diffusion bore 14 in the gas diffusion mechanism 16 has an S/l of 150 μm, for example, a monitor voltage (Vs)-output current (Is) characteristic is estimated in an oxygen gas of 1000 ppm. In this case, the results represented with solid lines 81, 82 as shown in FIG. 8 can be obtained. The solid line 81 represents the result when the conventional expression (1) is applied to the gas diffusion mechanism 16.

Figure 9:
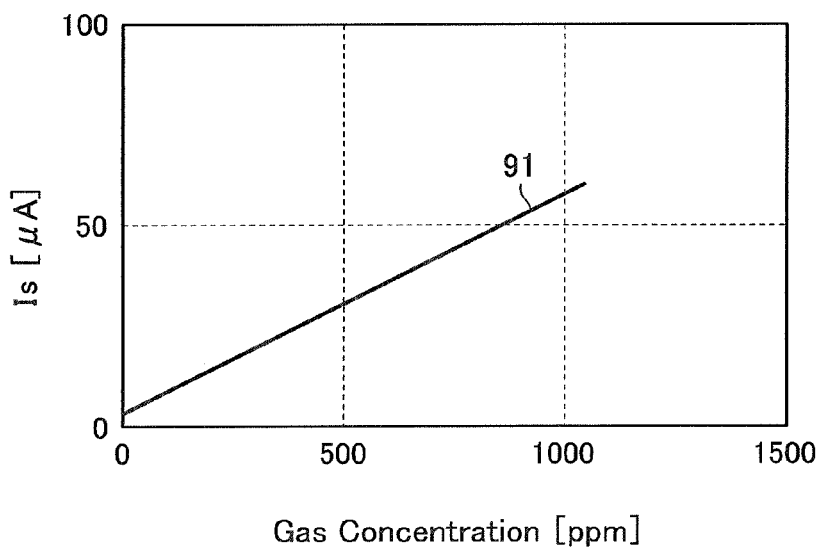
FIG. 9 is a graph showing a gas concentration characteristic of the limiting current type oxygen sensor.
Figure 10:
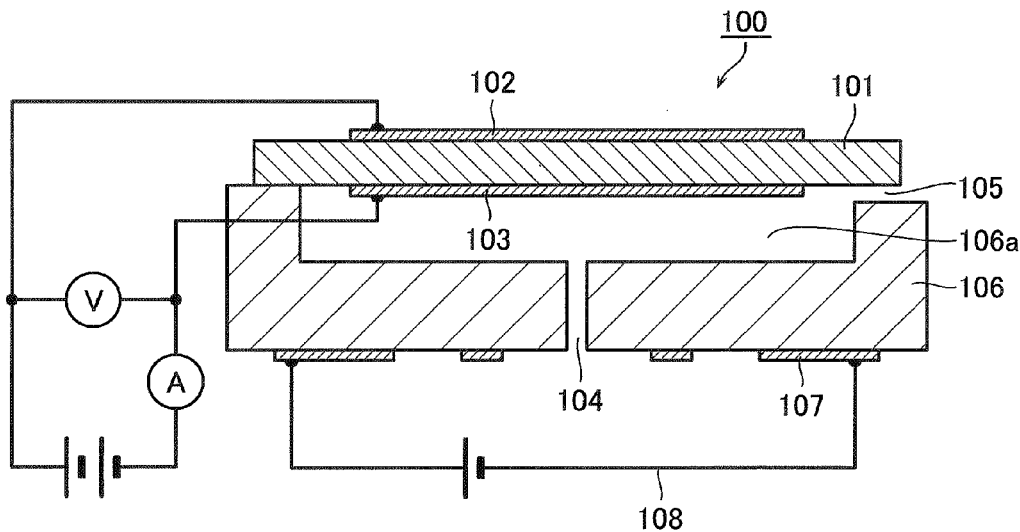
FIG. 10 is a schematic diagram showing a structure of a conventional limiting current type oxygen sensor.
Figure 11:
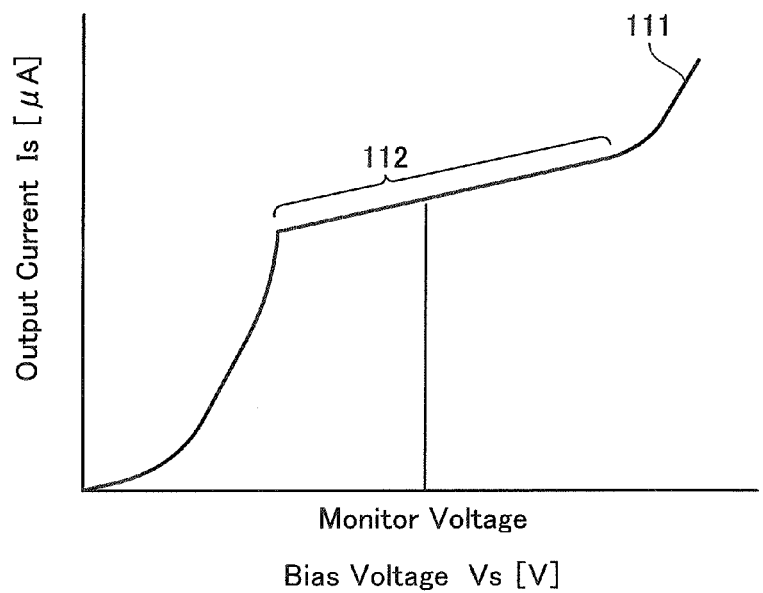
FIG. 11 is a graph showing a voltage (V)-current (I) characteristic of the conventional limiting current type oxygen sensor.

When the oxygen concentration gradient defined by the above-described expression (2) is applied to the gas diffusion mechanism 16 in this way, the output current value shown with the solid line 82 exhibits a lower value than the output current value shown with the solid line 81. When the oxygen concentration gradient defined by the expression (2) is applied, though, a flat zone 83 indicative of the limiting current can be obtained definitely. As shown in FIG. 9, when the oxygen concentration gradient of the expression (2) is applied within the internal space 15 in the gas diffusion mechanism 16 of the limiting current type oxygen sensor 10, a characteristic between the gas concentration and the output current having a linear relation as shown with a solid line 91 can be obtained.

Therefore, even at a low oxygen concentration of 1% or below, for example, the limiting current type oxygen sensor 10 according to the second embodiment of the present invention makes it possible to sense and measure the oxygen concentration accurately and excellently. The limiting current type oxygen sensor 10 according to the second embodiment of the present invention also makes it possible, as the gas diffusion bore 14 in the gas diffusion mechanism 16 is single, to achieve easy production in the production step, suppress variations in process accuracy characteristic and reduce production costs.

As described above, in accordance with the second embodiment of the present invention, the gas diffusion mechanism 16 of the limiting current type oxygen sensor 10 includes the gas diffusion bore 14 formed through the cap 13 toward the electrode 12a, and the internal space 15 brought into communication with the gas diffusion bore 14. The gas diffusion mechanism is configured such that the oxygen concentration gradient within the internal space 15 satisfies the above expression (2) as a certain condition. In addition, the thickness (lin) of the internal space 15 is formed, for example, larger than the bore diameter (Sl) of the gas diffusion bore 14. Therefore, it is possible to process the gas diffusion bore 14 easier and sense and measure the oxygen concentration accurately based on the oxygen concentration gradient that satisfies the certain condition. This make it possible to sense and measure an oxygen concentration accurately and excellently even at a lower oxygen concentration of 1% or below and to achieve easy producibility, prevent variations in process accuracy characteristic, and reduce production costs.

What is claimed is:

1. A limiting current type oxygen sensor, comprising:
   an ion conductor composed of a solid electrolyte;
   a porous electrode pair comprising a first electrode and a second electrode, wherein the ion conductor is disposed between the first and second electrodes and the porous electrode pair is adapted to apply an electric field between the first and second electrodes;
   a cap configured to supply a diffusion-rate-determined gas to a face of the first electrode; and
   a heater arranged to heat the ion conductor,
   wherein the cap includes an internal space in contact with the face of the first electrode, and a gas diffusion bore formed to communicate the internal space with a space outside of the cap, wherein the cap is configured such that an oxygen concentration gradient within the internal space satisfies the following expression:

$$1/I_{lim} = (1/4\,FDC_{o2})\{(l/S)+(l_{in}/S_{in})\}$$

which is based on a relationship between the Faraday constant (F); a diffusion coefficient (D); an oxygen concentration ($C_{o2}$); a bore area (S) of the gas diffusion bore; a bore length (l) in the axial direction of the gas diffusion bore; a distance ($l_{in}$) in the internal space between the first electrode and the inner surface opposed thereto; an effective cross section ($S_{in}$) of the internal space; and an output current value ($I_{lim}$);
   wherein the cap is configured such that the bore area (S) and the bore length (l) of the gas diffusion bore have a ratio (S/l) of 50-250 μm.

2. The limiting current type oxygen sensor according to claim 1, wherein the cap is formed such that the distance in the internal space between the first electrode and the inner surface opposed thereto is greater than or equal to the bore diameter of the gas diffusion bore.

3. The limiting current type oxygen sensor according to claim 1, wherein the cap is formed such that the distance in the internal space between the first electrode and the inner surface opposed thereto is greater than the bore diameter of the gas diffusion bore.

4. A method of sensing and measuring oxygen concentrations using a limiting current type oxygen sensor, the sensor including an ion conductor composed of a solid electrolyte, a porous electrode pair comprising a first electrode and a second electrode, wherein the ion conductor is disposed between the first and second electrodes and the porous electrode pair is adapted to apply an electric field between the first and second electrodes, a cap configured to supply a diffusion-rate-determined gas to a face of the first electrode, and a heater arranged to heat the ion conductor, the method comprising:
   forming in the cap an internal space in contact with the face of the first electrode, and a gas diffusion bore to communicate the internal space with a space outside of the gas diffusion mechanism; and
   sensing and measuring an oxygen concentration by executing a calculation such that an oxygen concentration gradient within the internal space satisfies the condition of the following expression:

$$1/I_{lim} = (1/4\,FDC_{o2})\{(l/S)+(l_{in}/S_{in})\}$$

which is based on a relationship between the Faraday constant (F); a diffusion coefficient (D); an oxygen concentration ($C_{o2}$); a bore area (S) of the gas diffusion bore; a bore length (l) in the axial direction of the gas diffusion bore; a distance ($l_{in}$) in the internal space between the first electrode and the inner surface opposed thereto; an effective cross section ($S_{in}$) of the internal space; and an output current value ($I_{lim}$);
   wherein the cap is configured such that the bore area (S) and the bore length (l) of the gas diffusion bore have a ratio (S/l) of 50-250 μm.

5. The method according to claim 4, wherein the internal space in the cap is formed such that a distance between the first electrode and an inner surface opposed thereto is greater than or equal to the bore diameter of the gas diffusion bore.

6. The method according to claim 4, wherein the internal space in the cap is formed such that a distance between the first electrode and an inner surface opposed thereto is greater than the bore diameter of the gas diffusion bore.

* * * * *